(12) United States Patent
Hunter et al.

(10) Patent No.: US 8,001,828 B2
(45) Date of Patent: Aug. 23, 2011

(54) MINIATURIZED METAL (METAL ALLOY)/PDO$_x$/SIC HYDROGEN AND HYDROCARBON GAS SENSORS

(75) Inventors: Gary W. Hunter, Oberlin, OH (US);
Jennifer C. Xu, Olmsted Township, OH (US); Dorothy Lukco, Sagamore Hills, OH (US)

(73) Assignee: The United States of America as represented by the Administrator of National Aeronautics and Space Administration, Washington, DC (US)

( * ) Notice: Subject to any disclaimer, the term of this patent is extended or adjusted under 35 U.S.C. 154(b) by 257 days.

(21) Appl. No.: 12/143,139

(22) Filed: Jun. 20, 2008

(65) Prior Publication Data

US 2009/0113992 A1    May 7, 2009

Related U.S. Application Data

(62) Division of application No. 11/434,578, filed on May 12, 2006, now Pat. No. 7,389,675.

(51) Int. Cl.
*G01N 27/00*    (2006.01)
(52) U.S. Cl. ........................ 73/31.06; 257/253
(58) Field of Classification Search .............. 73/31.06; 257/253
See application file for complete search history.

(56) References Cited

U.S. PATENT DOCUMENTS

| | | | |
|---|---|---|---|
| 3,671,414 A | 6/1972 | Grubb | |
| 3,709,810 A | 1/1973 | Grubb et al. | |
| 4,242,303 A | 12/1980 | Takahashi et al. | |
| 4,892,834 A | 1/1990 | Rauh | |
| 4,931,851 A | 6/1990 | Sibbald et al. | |
| 5,273,779 A | 12/1993 | Chen et al. | |
| 5,520,753 A | 5/1996 | Hunter | |
| 5,668,301 A | 9/1997 | Hunter | |
| 5,670,115 A | 9/1997 | Cheng et al. | |
| 5,783,153 A | 7/1998 | Logothetis et al. | |
| 6,027,954 A | 2/2000 | Hunter | |
| 6,109,094 A | 8/2000 | Baranzahi et al. | |

(Continued)

FOREIGN PATENT DOCUMENTS

JP    6-186191    7/1994

(Continued)

OTHER PUBLICATIONS

Chen, Liang-Yu et al, "Comparison of interfacial and electronic properties of annealed Pd/SiC and Pd/SiO2/SiC Schottky diode sensors",J. Vac Sci. Technol. A, May/Jun. 1997, pp. 1228-1234, 15 (3), American Vacuum Society.

(Continued)

*Primary Examiner* — Lisa Caputo
*Assistant Examiner* — Punam Roy
(74) *Attorney, Agent, or Firm* — Woodling, Krost and Rust; Robert H. Earp, III

(57) ABSTRACT

A miniaturized Schottky diode hydrogen and hydrocarbon sensor and the method of making same is disclosed and claimed. The sensor comprises a catalytic metal layer, such as palladium, a silicon carbide substrate layer and a thin barrier layer in between the catalytic and substrate layers made of palladium oxide (PdO$_x$). This highly stable device provides sensitive gas detection at temperatures ranging from at least 450 to 600° C. The barrier layer prevents reactions between the catalytic metal layer and the substrate layer. Conventional semiconductor fabrication techniques are used to fabricate the small-sized sensors. The use of a thicker palladium oxide barrier layer for other semiconductor structures such as a capacitor and transistor structures is also disclosed.

13 Claims, 9 Drawing Sheets

U.S. PATENT DOCUMENTS

| | | | |
|---|---|---|---|
| 6,160,278 | A | 12/2000 | Liu et al. |
| 6,184,564 | B1 | 2/2001 | Gould |
| 6,203,678 | B1 | 3/2001 | Leonhard et al. |
| 6,265,222 | B1 | 7/2001 | DiMeo, Jr. et al. |
| 6,291,838 | B1 | 9/2001 | Hunter |
| 6,342,712 | B1 | 1/2002 | Miki et al. |
| 6,635,913 | B2 | 10/2003 | Miki et al. |
| 6,730,270 | B1 | 5/2004 | O'Connor |
| 6,763,699 | B1 | 7/2004 | Hunter |
| 6,800,499 | B2 | 10/2004 | Chen et al. |
| 6,818,523 | B2 | 11/2004 | Miki et al. |
| 6,873,517 | B2 | 3/2005 | Nakamura |
| 6,935,158 | B2 | 8/2005 | Serina et al. |
| 7,389,675 | B1 | 6/2008 | Hunter et al. |
| 2004/0112764 | A1 | 6/2004 | Stokes et al. |
| 2005/0072673 | A1 | 4/2005 | Fukuda |
| 2005/0258051 | A1 | 11/2005 | Ono et al. |
| 2006/0038242 | A1 | 2/2006 | Hsu et al. |
| 2006/0270053 | A1 | 11/2006 | Tilak et al. |
| 2007/0209937 | A1 | 9/2007 | Hoagland et al. |

FOREIGN PATENT DOCUMENTS

| | | |
|---|---|---|
| JP | 7-260728 | 10/1995 |

OTHER PUBLICATIONS

Hunter, G. W. et al "SiC-Based Schottky Diode Gas Sensors", Materials Science Forum vols. 264-268, pp. 1093-1096, (1998), Trans Tech Publications Ltd, Switzerland.

Chen, Liang-Yu, et al. "Surface and Interface Study of PdCr/SiC Schottky Diode Gas Sensor Annealed at 425 C", NASA/TM-1998-107429, May 1998, NASA.

Hunter, G.W. et al. "Chapter 8 Case Studies in Chemical Sensor Development", BioNanoFluidic MEMS. p. 1 , pp. 199-233, Hesketh (ed.) Springer 2008.

Hunter, G. W. et al."Silicon Carbide Gas Sensors for Propulsion Emissions and Safety Applications" pp. 1-10, Presented at JANNAF Conference, May 14-17, 2007, Denver, Colorado, published Oct. 2007.

Chen, Liang-Yu, et al. "SiC-Based Gas Sensors", NASA Technical Memorandum 113125, pp. 1-16, Prepared for the 190th Meeting sponsored by the Electrochemical Society San Antonio, Texas Oct. 6-11, 1996 NASA.

Hunter, G.W. "An Overview of SIC Gas Sensor History" pp. 1-32, NASA Glenn Research Center Instrumentation and Controls Division Sensors and Electronics Branch Nov. 16, 2007.

Chen, Liang-Yu, et al. "Electronic and Interfacial Properties of Pd/6H-SiC Schottky Diode Gas Sensors" Third International High Temperature Electronics Conference (HiTEC), Jun. 9-14, 1996, pp. X-17-X-22, Transactions, vol. 1, Albuquerque, New Mexico USA.

Luongo, Kevin et al. "Development of a highly sensitive porous Si-based hydrogen sensor using PD nanostructures" Sens Actuators B 111-112 (2005) , 125-129.

JP7-260728. Derwent abstract in the English language.

JP6-186191. Derwent abstract in the English language.

Armgarth et al. Pd and Platinum Gate Metal-Oxide-Semiconductor Capacitors in Hyydrogen and Oxygen Mixtures, Appl. Phys. Lett., Oct. 1, 1982, 654-5, 41(7), Am. Inst. Phy.

Lundstrom et al.,"Chemical Sensors With Catalytic Metal Gates" J. Vac. Sci. Tech. A, May/Jun. 1996, 1539-45, 14(3), Am. Vac. Society.

Lundstrom,"Approaches and Mechanisms to Solid State Based Sensing", Sensors and Actuators B,1996, 11-19, 35-36, Elsevier Science S.A.

Hunter et al, "Chemical Gas Sensors for Aeronautic and Space Applications", NASA Tech. Memo. 107444, May 12, 1997,1-11,107444, NASA Lewis Research Center, Cleveland. Ohio.

Ekedahl et al.,"Hydrogen Sensing Mechanisms of Metal-Insulator Interfaces" Accounts of Chem. Research, May 2, 1998, 249-256, vol. 31, No. 5, American Chemical Society.

Hunter et al."Chemical Gas Sensors for Aeronautic and Space Applications II". NASA/TM—1998-208504, Oct. 1998, 1-13, 208504, NASA STI, Hanover, MD, USA.

Bohme et al. "Nanoparticles As the Active Element of High-Temp. Metal-Insulator-Silicon Carbide Gas Sensors" Adv. Mat., Apr. 18, 2001.597-601, 13( 8), Wiley-VCH, Weinheim, DE.

Hunter et al. "Development of SiC Gas Sensor Systems", NASA TM, Oct. 2002, 1-18, 2002-211707, NASA STI, Hanover, MD, USA.

Hunter et al. "Development of SiC-based Gas Sensors for Aerospace Applications", Mat. Res. Soc. Symp. Proc., 2004, J4.4.1-12, vol. 815, Materials Research Society.

Colinge et al. "Physics of Semiconductor Devices", 2002, 139-141, 144-147, 159-161, and 165-171, Kluwer Academic Publishers, AH Dordrecht, The Netherlands.

Neaman. "An Introduction to Semiconductor Devices", 224-228 and 423-426, 2006, The McGraw-Hill Companies, New York, NY.

Hunter, Gary W."Chemical Species Gas Sensors" Jan. 2004, pp. 1-5, http://www.grc.nasa.gov/WWW/chemsensors/.

Hunter, Gary W. "Structure of a Microfabricated Tin-Oxide Sensor" Nov. 2003, p. 1, http://www.grc.nasa.gov/WWW/chemsensors/tin-oxide.htm.

Neudeck, Phil, "Silicon Carbide Electronics" Dec. 21, 2005, pp. 1-2, http://www.grc.nasa.gov/WWW/SiC/SiC.html.

Hunter et al. "Development of Hydrogen Sensor Technology at NASA Lewis Research Center", NASA TM 106141, Nov. 1992, 1-19, 2002-106141, University of Cincinatti.

Stinespring, C.D. "Advanced Solid State Sensors for Vision 21 Systems Final Report", Apr. 28, 2005, 1-29, 2002-106141, West Virginia University, Morgantown, WV.

Lundstrom,"Why Bother About Gas-Sensitive Field Effect-Devices", Sensors and Actuators A 56,1996, 75-82, Elsevier Science S.A.

Lundstrom,"Natural Nanosystems", Current Applied Physics 2 (2002) 17-21, Elsevier Science S.A.

"How Semiconductors Are Made" Mar. 18, 2006, pp. 1-4, http://rel.intersil.com/docs/lexicon/manufacture.html, Intersil.

American Elements "Palladium Oxide", Mar. 27, 2006, p. 1, http://www.americanelements.com/pdox.html.

"How Light Emitting Diodes Work" http://electronics.howstuffworks.com/led1.htm, Feb. 24, 2006, pp. 1-3.

"How Semiconductors Work" http://electronics.howstuffworks.com/diode3.htm, Feb. 24, 2006, pp. 1-2.

Neudeck, Phil, et al. "High-Temperature Electronics—A Role for Wide Bandgap Semiconductors?", Proceedings of the IEEE, Jun. 2002, 1065-76, vol . 90, No. 6, IEEE.

"MOSFET", Wikipedia, Mar. 27, 2006, pp. 1-7, Wikipedia, http://en.wikipedia.org/wiki/MOSFET.

"High-k Dielectric", Wikipedia, Mar. 27, 2006, pp. 1-3, Wikipedia, http://en.wikipedia.org/wiki/High-k_Dielectric.

"Dielectric", Wikipedia, Mar. 27, 2006, pp. 1-3, Wikipedia, http://en.wikipedia.org/wiki/Dielectric.

"Palladium: compound data [palladium (IV) oxide]" Webelements, Mar. 27, 2006, pp. 1-4, http://www.webelements.com/webelements/compounds/text/Pd/O2Pd1-12036043.html?vo=1.

"Palladium: compound data [palladium (II) oxide]" Webelements, Mar. 27, 2006, pp. 1-4, http://www.webelements.com/webelements/compounds/text/Pd/O1Pd1-1314085.html.

DiMeo, Jr., Frank, "Integrated Micro-Machined Hydrogen Gas Sensor". DOE/GO/10451-F, Dec. 4, 2000, pp. 1-27, Department of Energy, USA.

Lundstrom, I "A Hydrogen-Sensitive MOS field-effect transistor". Applied Physics Letters, vol. 26, No. 2, Jan. 15, 1975, pp. 55-57, American Institute of Physics, 1975.

MINIATURIZED METAL (METAL ALLOY)/PDO$_x$/SIC HYDROGEN AND HYDROCARBON GAS SENSORS

This application is a Divisional Patent Application of U.S. patent application Ser. No. 11434,578 filed May 12, 2006 now U.S. Pat. No. 7,389,675 and claims the benefit of, and priority to, that application and its filing date.

ORIGIN OF THE INVENTION

The invention described herein was made by employees and by an employee of a contractor of the United States Government, and may be manufactured and used by the government for government purposes without the payment of any royalties therein and therefor.

FIELD OF THE INVENTION

The invention is in the field of hydrogen and hydrocarbon sensing. In particular hydrogen and hydrocarbon gas are detected using a microfabricated, miniaturized Schottky diode containing a stable interlayer of PdO$_x$ between a top catalytic sensing layer and SiC substrate.

BACKGROUND OF THE INVENTION

U.S. Pat. No. 5,670,115 to Cheng et al. discloses a thin film of palladium to catalyze the dissociation of Hydrogen gas. Detection and measurement of the hydrogen gas is accomplished with an amorphous metal film consisting of nickel and zirconium that has a resistance which varies with the concentration of dissolved hydrogen. This device consists of only two layers and operates in the range of room temperature to 150° C. According to Cheng, palladium film serves to dissociate hydrogen molecules at the Pd surface and the hydrogen atoms diffuse into the palladium film. Hydrogen atoms diffuse through the thin palladium film into the underlying nickel-zirconium film and dissolve therein. Hydrogen atoms flow into and out of the films depending on the hydrogen gas concentration. The electrical resistivity of the nickel-zirconium film increases as the content of the dissolved hydrogen increases. The palladium layer also serves as a barrier to oxidation of the underlying nickel-zirconium film. See, the '115 patent to Cheng at col. 2, lns. 1 et seq.

U.S. Pat. No. 3,709,810 to Grubb et al. discloses the use of an improved hydrogen ion selective sensing electrode comprising a palladium oxide coated surface on a palladium coated base member along with a reference electrode in contact with an electrolyte chamber.

U.S. Pat. No. 6,184,564 to Gould discloses a Schottky diode having a palladium silicide on silicon barrier in which the barrier height is adjusted by adding a small quantity of another metal during the deposition of the palladium. The palladium silicide includes palladium and a small quantity of another metal. The additional metal is chosen depending on whether barrier height is raised or lowered. See col. 1, lns. 59 et seq of the '564 patent to Gould. Gould does not mention hydrogen detection.

U.S. Pat. No. 5,783,153 to Logothetis et al. discloses a sensor made from a metal or its oxide which is capable of changing from one metal or metal oxide phase to another. The oxygen sensitive material disclosed is palladium which changes phase to palladium oxide when the partial pressure of oxygen reaches a certain value. This phase change causes a change in the material's conductivity which can be measured.

U.S. Pat. No. 6,818,523 to Miki et al. teaches the method for producing a semiconductor storage device comprising a hydrogen diffusion preventing layer. The semiconductor storage device comprises a capacitor electrode with a film to reduce the amount of hydrogen reaching the capacitor electrode. Miki discloses the use of palladium oxide as a hydrogen diffusion preventing layer. See FIG. 3 wherein Miki et al. discloses a diffusion layer 302. Miki at col. 3 lns. 24 et seq. and at col. 7, lns. 45 et seq. identifies palladium oxide as preventing hydrogen diffusion. Miki et al. uses capacitors comprising stacked layers and palladium oxide as a conductor and not as a dielectric.

U.S. Pat. No. 6,730,270 to O'Connor discloses a single-chip hydrogen sensor wherein a silicon-based hydrogen sensor portion is comprised of a first material and an interconnect metallization layer of the same material. The first material taught in the application is a palladium nickel alloy. The interconnect metallization is covered with an oxide or a nitride to make the interconnect metallization inert. See col. 2 lns. 21-36.

U.S. Pat. No. 6,109,094 to Baranzahi et al. teaches the use of a gas sensing device having a semiconductor substrate wherein the semiconductor substrate is covered by an insulator layer on which an intermediate layer is formed, and is subsequently covered by a gas sensing catalytic layer. The semiconductor substrate disclosed in this patent is silicon carbide or diamond. The intermediate layer is a silicide. The device can be operated at 600° C. continuously. Baranzahi et al. indicates at col. 4 lns 27 et seq. that the voltage-capacitance curve shifts for a MOSiC device.

FIG. 1 illustrates a Pd/SiO$_2$ hydrogen sensor 100 illustrated in an article entitled "Hydrogen Sensing Mechanisms Of Metal-Insulator Interfaces," Acc. Chem. Res. 1998, 31, pp. 249-256, by LARS-GUNNAR EKEDAHL, MATS ERIKSSON, and INGEMAR LUNDSTROM. FIG. 1 illustrates a catalytic metal Pd which dissociates molecular hydrogen into atomic or elemental H$^+$ which then forms a dipole layer at the interface of the Pd 103 and the SiO$_2$ 104. SiO$_2$ is an insulator and a Si substrate 105 is used and is interconnected to ground 102. A voltage 101 is supplied across the device which functions as a capacitor.

FIG. 1A illustrates 100A a shifting of the voltage-capacitance curve as a function of the hydrogen content. As the hydrogen content increases the magnitude of the CV shift or ΔV increases in proportion to the charge concentration and separation (for example, the dipole moment) as set forth on page 250 of the reference cited immediately hereinabove. Reference numeral 106 represents the CV curve without the presence of hydrogen and reference numeral 107 represents the CV curve with the presence of hydrogen.

FIG. 1B illustrates 100B the dipole layer 104A formed at the interface of the Pd and the insulator SiO$_2$. Hydrogen (H$_2$) 109 is dissociated into atomic hydrogen (H$^+$) and the magnitude of the dipole layer is dependent on the amount of hydrogen available.

An article entitled "PHYSICS WITH CATALYTIC METAL GATE CHEMICAL SENSORS", VOL. 15, Issue 3 (1989) by Ingemar Lundstrom, Marten Armgarth, and Lars-Gunnar Petersson, also discloses the palladium-silicon dioxide-silicon capacitor and other structures.

U.S. Pat. No. 6,265,222 to DiMeo, Jr. et al. teaches the use of a hydrogen sensor including a hydrogen-interactive metal film that reversibly interacts with hydrogen to exhibit a detectable change. A thin film hydrogen permeable barrier layer is used to protect the hydrogen interactive layer from deleterious interaction with non-hydrogen species. DiMeo discloses the use of palladium as the thin film permeable barrier and rare earth metals as the hydrogen interactive layer.

In an article authored by Frank DiMeo Jr., PhD., entitled "Integrated Micro-Machined Hydrogen Gas Sensor" prepared for and sponsored by the United States Department of Energy, DOE/GO/10451-F, a recountal of existing hydrogen sensing technology is found. The article discloses (at page 5 thereof) a gated field effect type transistor like structure having a floating gate that is coated with a catalyst, typically palladium. As the palladium gate adsorbs hydrogen the potential of the gate changes and modulates the conductance of the channel. Dr. Dimeo goes on to indicate that the device is quite sensitive but tends to saturate at low levels of hydrogen making it unsuitable for explosive limit detection. The article goes on to discuss another hydrogen sensor which is based on resistivity changes that occur as a function of hydrogen content in palladium or palladium alloys. Dr. DiMeo does not indicate the structure of these devices and claims that they were not sensitive.

The article entitled "Development of SiC-based Gas Sensors for Aerospace Applications", *Mat. Res. Soc. Symp. Proc. Vol.* 815, 2004 by G. W. Hunter et al. discloses the use of chrome carbide as a barrier layer between the catalytic metal and the SiC semiconductor. Although this composition showed no indication of massive silicide formation between the catalytic sensing layer and the semiconductor substrate, this sensor showed limited sensitivity to hydrogen and showed signs of chromium migration to the surface as well as formation of chromium oxide.

Use of catalytically active resistors is based on the concept that hydrogen migrates into the resistor and changes the resistance of the sensor. Palladium and its alloys are common resistor materials. The use of palladium as the hydrogen sensitive metal is problematic because a phase change occurs at high hydrogen concentrations. Use of palladium, however, at low hydrogen concentrations does not cause a phase change to occur and Pd alloys can be used for higher hydrogen concentration measurements. See the article entitled "The Development of Hydrogen Sensor Technology at NASA Lewis Research Center, NASA"-Technical Memorandum-106141 (1992) by G. W. Hunter et al.

There is a growing demand for high temperature gas sensors with high sensitivity for engine emission monitoring, fire detection, and fuel leak detection. In particular, high temperature gas sensors with high sensitivity are of interest for aerospace applications including: monitoring emissions from high temperature combustion systems or chemical processing applications, monitoring of fuel leaks in launch vehicles, and fire detection on-board commercial and space vehicles.

A Schottky diode sensing structure can be used to measure hydrogen concentration due to its high gas sensitivity. A Schottky diode can be generally defined as a metal in contact with a semiconductor (MS) or a metal in contact with a thin insulator (MIS) or oxide (MOS) on a semiconductor.

Hydrogen ($H_2$) dissociates on the surface of the metal leading to the formation of a dipole layer at the interface of the metal and the semiconductor lower layer. The dipole layer leads to a change in the forward or reverse current and a change in the capacitance. The height of the potential barrier is a function of the materials used and their temperature. See the article entitled "Development of SiC Gas Sensor Systems," NASA/TM-2002-211707 by Hunter et al. The barrier height depends on the work function of the metal and the electron affinity of the semiconductor. Further, use of a Schottky diode allows hydrogen to be detected without requiring high voltage. A small change in the concentration of hydrogen can be reliably detected.

The article entitled "Development of SiC Gas Sensor Systems", NASA/TM-2002-211707, by G. W. Hunter et al. discloses two structures to improve the stability of the palladium based Schottky diode structures over that of the Pd/SiC Schottky sensor. The first structure includes the incorporation of chemically reactive oxides such as $SnO_2$ (tin oxide) for a MOS device. SiC devices can be operated at high temperature to be reactive to hydrocarbons resulting in a MROS (metal reactive oxide semiconductor). Tin oxide ($SnO_2$) is recited in the article as a reactive oxide. The second structure is PdCr/SiC which has shown good response and stability for some samples but for others has the drawback of silicide formation at the interface of the metal and the semiconductor. The article also mentions a wide variety of materials sensitive to hydrocarbons that may be used without specifying them.

The temperature range for hydrogen detection as is identified hereinabove is beyond the upper limit for substrates made from Silicon-based semiconductor substrates. The use of silicon carbide allows for hydrogen detection in the demanding range of conditions required in aerospace applications. Although silicon carbide has excellent high temperature performance, the sensitivity of the device is limited by the reliability and stability of the interfaces between the silicon carbide semiconductor substrate layer and the other layers of the device. At high temperatures, reactions between the various different layers can lead to the formation of silicide materials. These reactions lead to reduced sensitivity and disruptions of the device. The reaction between the layers is a problem for high temperature application requirements where it is difficult to optimize both sensitivity and stability of the device.

In addition to diodes, other devices including capacitors, Metal-Oxide-Semiconductor-Field-Effect-Transistors (MOSFETS), Metal-Semiconductor Field Effect Transistor (MESFET), and Metal-Insulator-Semiconductor Field Effect Transistor (MISFET) are used as gas sensors. Catalytic metals are used as gates for gas sensitive field effect devices. In addition to the gate, these devices typically contain electrodes, a source and a drain, interconnected by a channel region. The channel carries current between the source and the drain. Varying potential of the gate affects the amount of current flowing in a MESFET structure. In MISFET devices, a gate insulator material is located between the gate electrode and the channel.

Generally, a metal oxide is located between the gate electrode and the channel in a MOSFET structure. Use of a catalytic sensing metal, for example palladium, in the gate allows hydrogen detection to occur when the hydrogen gas is disassociated into atomic hydrogen and adsorbed onto and into the catalytic sensing metal causing a change in the electronic properties of the device.

A description of electronic semiconductor based gas sensors including MOS (metal oxide semiconductors), MIS (metal insulator semiconductors) and MRIS (metal reactive insulator semiconductor) technology can be found in articles entitled "Chemical Gas Sensors for Aeronautics and Space Applications," NASA Technical Memorandum 107444, May 1997 and in "Chemical Gas Sensors for Aeronautics and Space Applications II," NASA Technical Memorandum, 1998-208504, 1998.

At high temperatures many gas detecting sensors are not able to maintain sensitivity and stability due to chemical reactions occurring between the catalytic metal sensing layer and substrate layer or between the catalytic sensing layer, barrier layer, and substrate layer. Typically, reactions between the layers of the gas detecting device can lead to the formation of metal silicides on the interface between the metal or metal alloy layer and the substrate layer. The silicide materials which may form render the overall sensor insensitive to hydrogen and hydrocarbon materials. As a result, formation of silicide materials leads to decreasing hydrogen and hydrocarbon detection sensitivity, undesired oxidation, disruption, and degradation of the sensor device. Silicides are understood to incapacitate the sensor. At the same time, to be an effective hydrogen gas detector it is important for the sensor to be able to function at temperatures as high as 600° C. without interruption.

A further problem found in the prior art (Logothetis et al., U.S. Pat. No. 5,783,153) is hysteresis which contributes to the decreasing accuracy of the device at high temperatures. It is known that some metals react with oxygen resulting in the formation of a metal oxide. However, one form of metal oxide can change to another metal oxide phase when the temperature or atmosphere is changed. The different oxidation states of a metal or metal alloy also can result in changes in the resistivity of the metal or metal alloys. Hysteresis is related to phase changes between states brought on by chemical reactions leading to nonreversible changes. Hysteresis can lead to longer response times in the sensor and damage to the metal film used in the device. Phase changes can lead to problems which can affect both the sensitivity and stability of the sensor.

SUMMARY OF THE INVENTION

A new gas sensing structure and method of making same is disclosed and claimed. Ideally, the gas sensor is intended to operate in the absence of oxygen, but it may be used if oxygen is present. Ideally, the sensor is intended to operate with hydrogen concentrations of at least between 0 to 4%. However, the principles of the invention are applicable to use at hydrogen concentrations in the range of 0 to 100% hydrogen by alloying the catalytic metal with another metal if necessary. The gas sensing structure comprises a catalytic sensing layer, a substrate layer, and a barrier interlayer located in between the catalytic sensing layer and the substrate layer. The catalytic sensing layer is made up of a metal or metal alloy that is sensitive to hydrogen and hydrocarbons. The catalytic sensing layer can be made from a metal or metal alloy, specifically a metal selected from the group consisting of Pt, Pd, Au, Ir, Ag, Ru, Rh, In, Os, Cr, and Ti. The catalytic sensing layer can also be made from a metal alloy, specifically a metal alloy made from at least two metals selected from the group consisting of Pt, Pd, Au, Ir, Ag, Ru, Rh, In, Os, Cr, and Ti. The catalytic sensing layer contains material capable of dissociating hydrogen gas ($H_2$) and hydrocarbon gas into atomic hydrogen ($H^+$). The resulting hydrogen is adsorbed onto the surface of the catalytic sensing layer and into the catalytic sensing layer producing a change in an electrical property of the catalytic sensing layer which varies with the concentration of hydrogen.

When a palladium/palladium oxide/silicon carbide diode is formed it is understood that the effective work function of the Palladium changes and hydrogen forms a dipole layer at the catalytic metal/palladium oxide interface as the hydrogen content increases resulting in an increase of the current within the diode for a given applied voltage across the diode. A forward or reverse bias may be applied to the diode. When the invention is used in the form of a diode an extremely thin layer of palladium oxide is employed which permits electron tunneling and conduction through the palladium oxide. The use of extremely thin layers such as is disclosed herein in thicknesses between 50 to 200 Angstroms allows conduction by tunneling.

When a palladium/palladium oxide/silicon carbide capacitor is formed the palladium oxide layer is significantly greater than 200 Angstroms thick and is non-conductive. As the hydrogen concentration of the hydrogen-laden palladium layer increases, the capacitance for a given applied voltage changes (or shifts). The shift is due to the dipole which is created at the interface of the palladium and palladium oxide.

When a palladium/palladium oxide/silicon carbide capacitor is arranged as a MOSFET (metal oxide semiconductor field effect transistor) the palladium oxide layer is greater than 200 Angstroms thick and is non-conductive. As the hydrogen concentration of the hydrogen-laden palladium layer increases, the capacitance for a given applied voltage changes (or put another way shifts) which modulates the current flow between the source and the drain in a channel in the n-type epilayer of the silicon carbide substrate. A voltage is applied across the source and drain. The source and drain are sometimes referred to herein as the first and second electrodes.

The substrate layer consists of an n-type semiconductor such as n-type silicon carbide. The excellent high temperature properties of silicon carbide enable it to serve as a durable substrate in the device for high temperature applications in the range of at least 450-600° C.

The barrier interlayer consists of a stable material to prevent unwanted reaction products between the catalytic sensing layer and the substrate layer at high temperatures. The barrier interlayer consists of palladium oxide, a highly stable metal oxide. The palladium oxide is applied by standard deposition techniques. $PdO_x$ can form naturally from Pd in Pd based gas sensors and can disrupt the gas sensor when formed in-situ in a highly uncontrolled manner. However, when palladium oxide is applied in a controlled manner by standard deposition techniques, an effective layer is created which prevents the formation of silicides.

The use of $PdO_x$ was discovered by observing the oxidation and degradation of PdCr on SiC gas sensing structures. After being heated in air at high temperature, metal silicides, $PdO_x$ and $Cr_xO_y$ can form from the PdCr/SiC sensor. The $Cr_xO_y$ migrated toward the sensor surface but it was observed that any $PdO_x$ that formed and remained at the interface appeared to prevent further formation of metal silicides. The $PdO_x$ layer that was formed by PdCr reacting in an oxidizing environment in an uncontrolled process did not prevent disruption of the sensor structure leading to sensor degradation. However, it was found that placing $PdO_x$ in the structure in a controlled and uniform manner provides a stable barrier layer that does not degrade in oxidizing environments and prevents formation of metal silicides. The fabrication of one Schottky diode sensor included the controlled sputter deposition of 50 Angstroms of $PdO_x$ on a SiC substrate and deposition of 450 Angstroms of Pt on top of the $PdO_x$. The polytype 6H—SiC semiconductor (approximately 400 microns thick) was used although it is believed the same chemical behavior would be seen with other polytypes such as 4H or 3C.

The SiC substrate (400 microns in thickness) is deposited with backside contact Ti and Ni first, the substrate can then be patterned with photoresist and a Schottky diode photomask to form the desired diode pattern examples disclosed herein. After deposition of $PdO_x$ and the gate metals/metal alloys, a lift-off process completes the Schottky diode fabrication. The result, based on testing, was a high sensitivity $Pt/PdO_x/SiC$ sensor with prolonged stability and represents a marked improvement over a Pt/SiC Schottky diode sensor which did not have the $PdO_x$ layer. Surface analysis was conducted on the tested $PdO_x$ based sensor and no significant silicide formation was observed. In other words, this implies that two of the major reasons for sensor degradation, silicide formation and migration, are significantly inhibited.

The barrier layer of $PdO_x$ prevents and minimizes chemical reaction between the catalytic sensing layer (metal or metal alloy) and the substrate layer (SiC). This approach takes a reaction product whose formation previously contributed to the disruption of the sensor structure and by controlling its formation and position in the gas sensor structure uses it to improve sensor stability and sensitivity. The $PdO_x$ layer is very stable and is potentially reduced to Pd through combination with atomic hydrogen. It is believed, but has not yet been verified, that this would likely increase the sensitivity of the device by creating more Pd. Oxidation of the barrier layer which is sometimes problematic with other barrier layers is not an issue with $PdO_x$ because it is already oxidized.

Palladium oxide prevents formation of metal silicides, an unwanted reaction product which forms between the catalytic sensing layer and the substrate layer. These silicide materials can adversely affect the sensitivity of the hydrogen detection.

Gas sensors with high sensitivity necessary for engine emission monitoring, fire detection, and fuel leak detection must be stable for operation at temperatures at least from 450 to 600° C. With the use of palladium oxide as a barrier layer between the catalytic sensing layer (metal layer) and the substrate layer (semiconductor), formation of metal silicides can be prevented while maintaining high sensitivity and prolonged stability of the device.

A method for making the gas sensor is also disclosed and claimed. The steps for making a gas sensing diode include: preparing an n-type substrate such as n-type silicon carbide (SiC) by cleaning, patterning with a photoresist/mask pattern and depositing backside contacts; depositing the barrier interlayer through the use of controlled reactive sputter deposition or evaporation of approximately 50 Angstroms of Palladium in oxygen/argon gases on said n-type SiC forming $PdO_x$; and, sputter deposition of the catalytic sensing layer approximately 450 Angstroms thick on top of the barrier interlayer. The method for making a MOSFET includes application of photoresist, masking, and etching to provide the intended structure. Alternatively, the palladium oxide may be produced by wet chemistry.

A method for using the hydrogen or hydrocarbon gas sensor present at high temperatures is also disclosed and claimed. The method comprises the steps of: applying a bias voltage across the top contact and bottom contact layers of a Schottky diode where the diode is comprised of a top metal or metal alloy layer, an n-type substrate layer, and a barrier interlayer comprising a palladium oxide located between the metal or metal alloy layer and substrate layer, and, measuring the current in gaseous hydrogen or hydrocarbons. Methods for using the invention in the form of a capacitor (MOS) and in the form of a transistor (MOSFET) are also disclosed herein.

The gas sensing structure has been developed for detection of hydrogen or hydrocarbon gas at temperatures in the range of at least 450-600° C. The stable composition of gas sensing structure prevents unwanted reaction between the catalytic sensing layer and the substrate layer at higher temperatures. Disruption of the operation of the device at high temperature due to the formation of metal silicides and oxidative degradation of the sensor is also prevented.

The layers of the device are assembled as a miniaturized Schottky diode hydrogen and hydrocarbon sensor. The sensor has high sensitivity based on the stability of the barrier interlayer which prevents unwanted reactions between the catalytic sensing layer and the substrate layer. Detection of extremely low levels of hydrogen gas and hydrocarbon gas is possible due to the high sensitivity of the device. Optimal voltage levels can be used without requiring high voltage to detect hydrogen or hydrocarbon gas. The sensor of the present invention is a high gain device.

The miniaturized Schottky diode hydrogen and hydrocarbon sensor with the structure of catalytic sensing layer—barrier interlayer—substrate (metal-metal oxide-silicon carbide) is fabricated with semiconductor microfabrication techniques. The inclusion of the palladium oxide barrier interlayer between the catalytic metal layer and the substrate layer allows for a device that has long term stability at high temperatures while maintaining high sensitivity and fast response time. The device is small in size and easy to fabricate. Semiconductor wafer chip mass-fabrication can be used to produce the device cost effectively. Further, the unique structure of the device including its high sensitivity, stability, and small-size allows for effective and versatile use in numerous applications.

It is an object of the present invention to provide a miniaturized Schottky diode hydrogen and hydrocarbon sensor with the structure of catalytic metal layer-palladium oxide barrier interlayer-silicon carbide (SiC) substrate layer.

It is a further object of the present invention to provide a miniaturized Schottky diode hydrogen and hydrocarbon sensor having a stable and sensitive palladium oxide barrier layer.

It is a further object of the present invention to provide a miniaturized Schottky diode hydrogen and hydrocarbon sensor capable of operating in the temperature range of at least 450-600° C.

It is a further object of the present invention to provide a sensor structure that is able to be used in a variety of electronic measurement applications where high stability, high sensitivity, and small size are required.

It is a further object of the present invention to provide a material which is stable at high temperatures and prevents reactions between a catalytic sensing layer and the substrate layer of a sensor at high temperatures.

It is a further object of the present invention to provide a material for use in a sensor which is sensitive to hydrogen gas and gaseous hydrocarbons and resistant to oxidative degradation at high temperatures.

It is an object of the present invention to provide a hydrogen sensor which does not form silicides that migrate throughout the device.

It is an object of the present invention to provide a Schottky diode comprising a catalytic metal on top of a palladium oxide interlayer which is sandwiched between the catalytic metal and the semiconductor.

A better understanding of these and other objects of the invention will be had when reference is made to the Brief Description Of The Drawings and the Claims which follow hereinbelow.

A better understanding of the drawings and invention will be had when reference is made to the Description of the Invention and Claims which follow hereinbelow.

DESCRIPTION OF THE INVENTION

The present invention comprises a miniaturized Schottky diode hydrogen and hydrocarbon sensor with the structure of catalytic sensing metal-palladium oxide barrier interlayer-semiconductor substrate layer to detect hydrogen and hydrocarbon gases at elevated temperatures. The metal-metal oxide-semiconductor structure provides a stable and sensitive hydrogen gas detection device that is resistant to oxidative degradation and silicide formation. The sensitivity of the device is achieved through the use of a metal such as platinum or palladium in the catalytic sensing layer which is sensitive to hydrogen and hydrocarbons but resistant to significant oxidation. The barrier interlayer is resistant to oxygen and prevents reaction between the catalytic sensing metal layer and the semiconductor substrate layer. These unwanted reactions lead to the formation of silicides which affect the surface states of the SiC interface. As a result, formation of silicide can lead to disruption of the layers and reduce the overall performance of the device including reduced sensitivity and stability. The palladium oxide barrier interlayer allows stable operation of the device at high temperatures as a voltage is applied across the top and bottom layers of this device. By stability, it is meant that a significant chemical reaction between the catalytic metal layer and the semiconductor substrate does not occur. By barrier it is meant a chemical barrier not to be confused with the term potential barrier which is relevant to the metal-semiconductor junction of a Schottky diode.

The catalytic sensing layer shows changes in the current voltage curve in the diode application and/or changes in capacitance for a given voltage in the MOS capacitor or MOSFET transistor applications.

Figures 1, 1A, 1B:
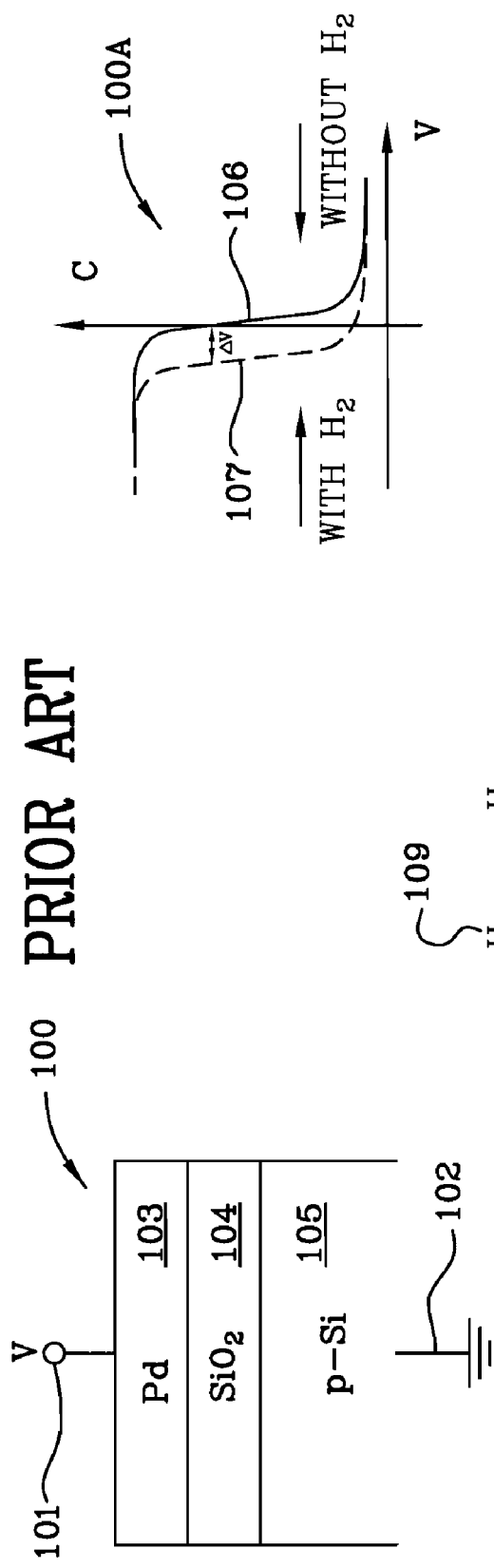
FIG. 1 is a schematic presentation of a prior art $Pd/SiO_2/Si$ hydrogen sensor.
FIG. 1A is a capacitance versus voltage plot of the sensor of FIG. 1.
FIG. 1B is a schematic representation of the dipole formed at the interface of the Pd and the $SiO_2$.
Figure 2:
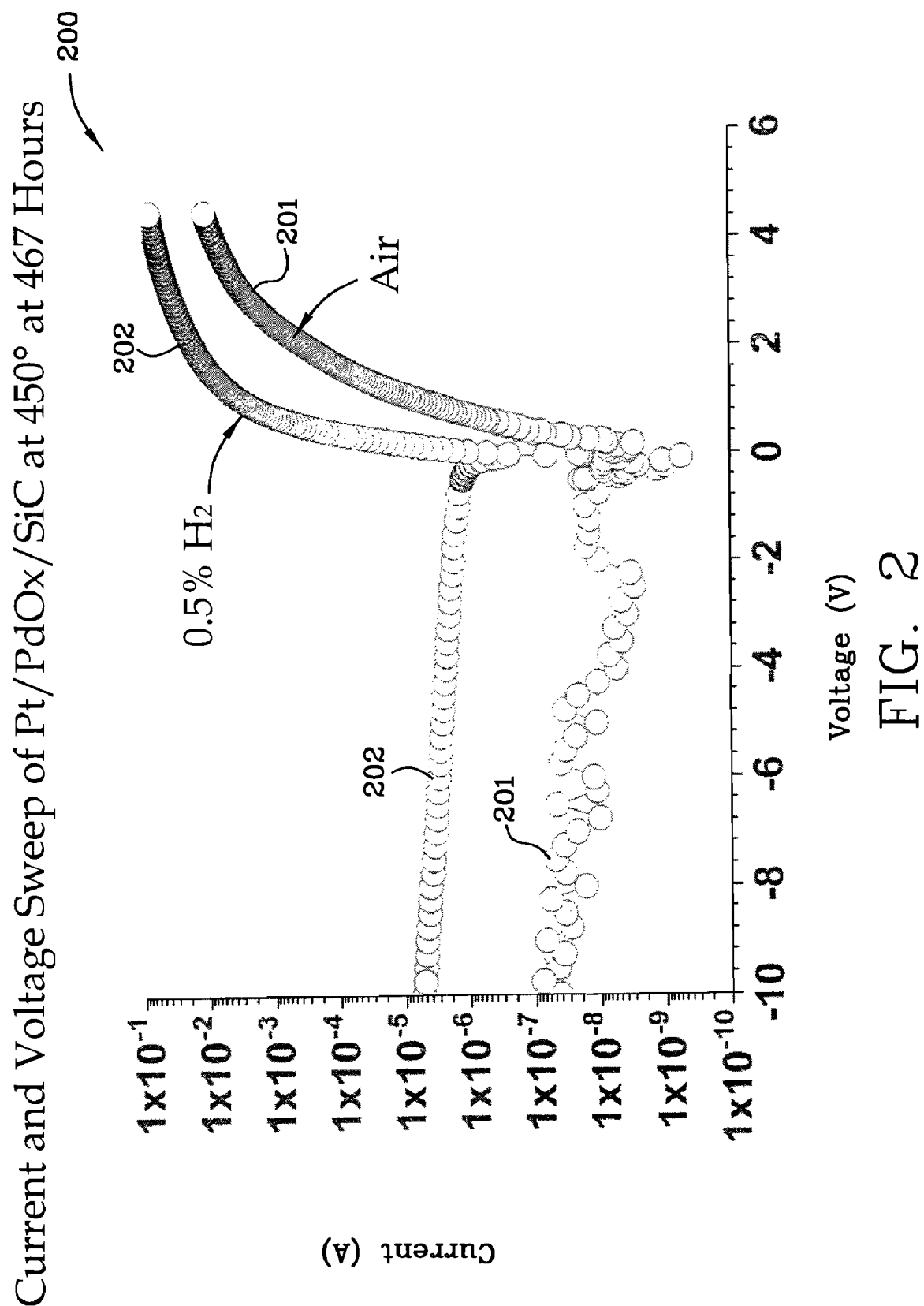
FIG. 2 is a current and voltage sweep of the $Pt/PdO_x/SiC$ hydrogen diode sensor of the instant invention.

FIG. 2 is a current and voltage sweep 200 of a Pt/PdO$_x$/SiC hydrogen diode sensor of the instant invention at 450° C. at 467 hours of operation. The current in air is denoted by reference numeral 201 and the current in an atmosphere of 0.5% hydrogen gas with the balance being nitrogen is denoted by reference numeral 202. From FIG. 2 it can be seen that the gain in the reverse bias sense is stable (approximately constant) between voltages of 0 and −10 VDC. It can also be seen that high gain and high current outputs are achieved when forward bias is applied. Gain is defined here as the current output of the sensor in hydrogen divided by the current output of the sensor in air. The sensitivity of the device is high with sensitivity being defined here as the change of the output in hydrogen as compared with air.

Figure 2A:
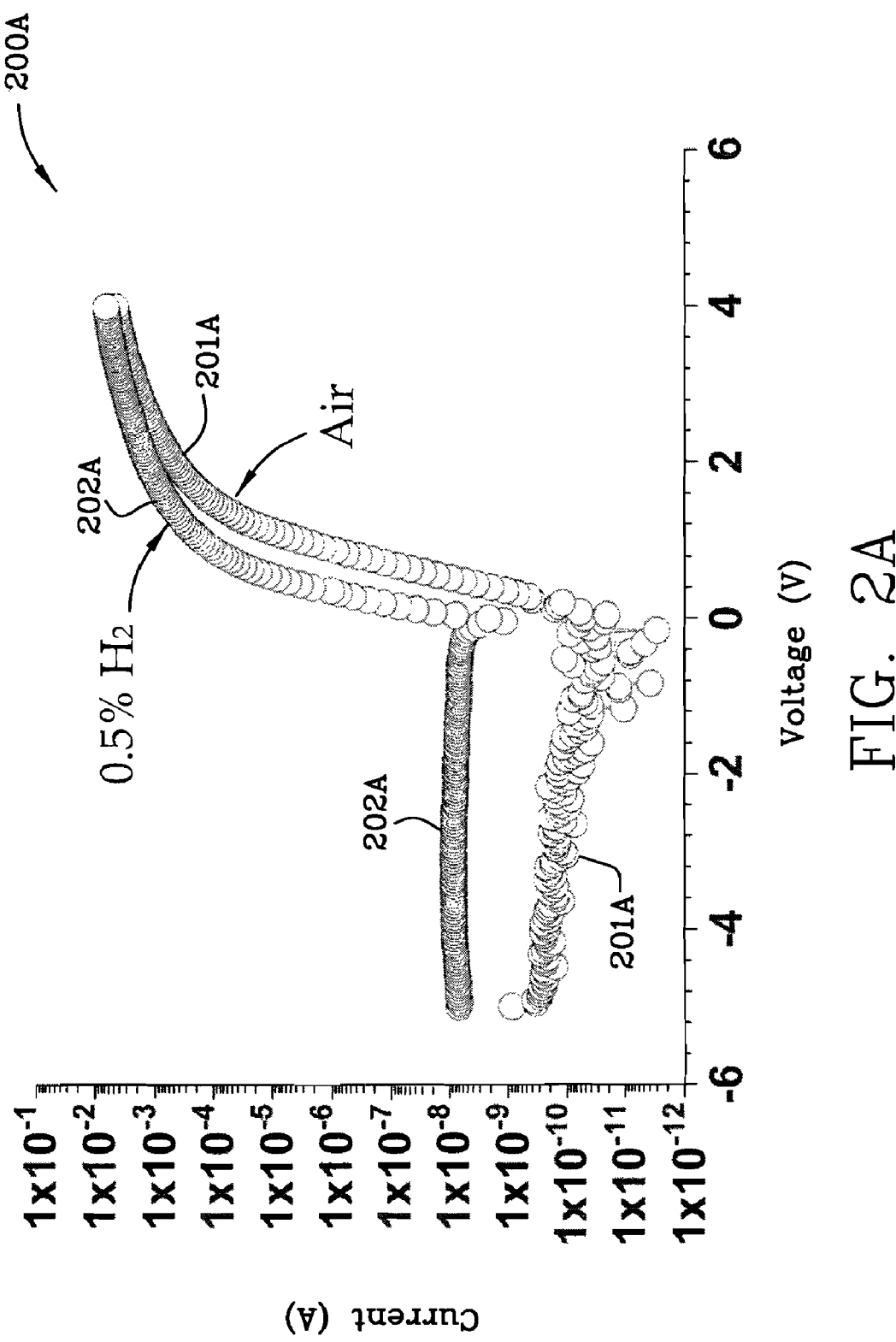
FIG. 2A is a current and voltage sweep of the $Pd/PdO_x/SiC$ hydrogen diode sensor of the instant invention.

FIG. 2A is a current and voltage sweep 200A of the Pd/PdO$_x$/SiC hydrogen diode sensor of the instant invention at 450° C. at 715 hours of operation. The current in air is denoted by reference numeral 201A and the current in an atmosphere of 0.5% hydrogen gas with the balance being nitrogen is denoted by reference numeral 202A. From FIG. 2A it can be seen that the gain in the reverse bias sense is stable (approximately constant) between 0 and −6 VDC. It can also be seen that high gain and high current outputs are achieved at the threshold voltage in the forward bias sense yielding a similar high gain and sensitivity. Gain is defined here as the current output of the sensor in hydrogen divided by the current output of the sensor in air.

Figure 3:
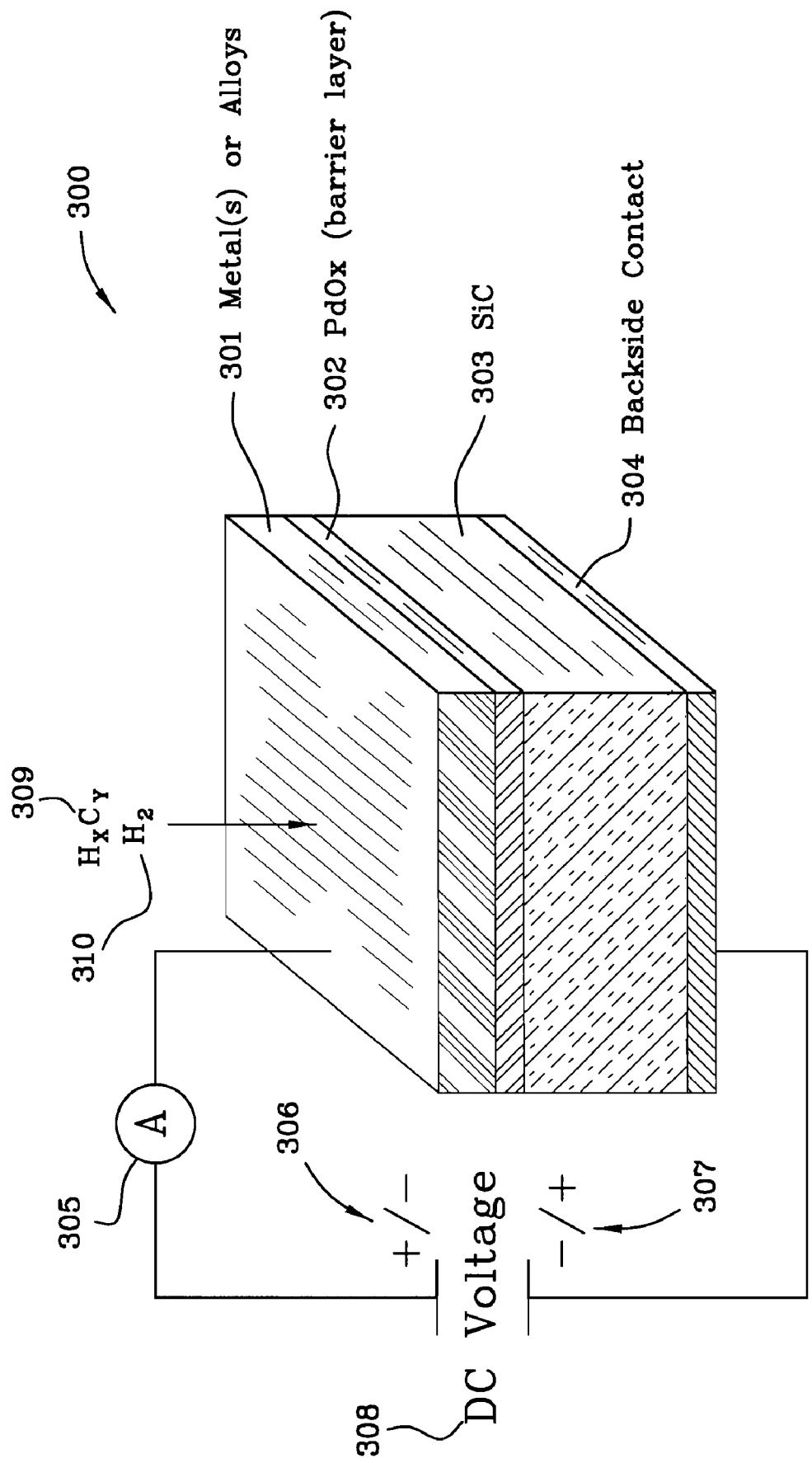
FIG. 3 is a cross-sectional view of the invention illustrating the catalytic metal layer, the palladium oxide barrier interlayer, and the substrate layer with an applied direct current voltage.

FIG. 3 is a cross-sectional view of the gas detecting device 300 illustrating the metal(s) layer 301, the PdO$_x$ (barrier layer) 302, and the Silicon Carbide 303 (substrate layer) with an applied direct current voltage 308. Backside contact 304 leads to the voltage source. Reference numerals 306/307 indicated that the polarity of the voltage may be changed across the diode if a reverse bias is desired as illustrated in FIG. 2. The catalytic sensing metal is located directly on top of the barrier interlayer and is in complete contact with the barrier layer. The catalytic sensing metal has a thickness of approximately 450-500 Angstroms but could be as thick as 1000 Angstroms. The barrier interlayer is located next to the catalytic sensing material and is approximately 50 Angstroms thick in the diode embodiment. This enables electron tunneling and electrical conduction to occur through the diode in either a forward direction or a reverse direction. Palladium oxide is understood to be non-conductive unless used in extremely thin applications such as the instant application being 50 Angstroms thick. An amp meter 305 measures the current in the diode. The detection voltage in the forward bias sense is approximately 0.3 to 1.0 VDC. Hydrogen and/or hydrocarbons are represented by reference numerals 310 and 309, respectively.

The semiconductor used herein is preferably of the polytype known as 6H, 4H or 3C—SiC which has surface characteristics conducive to receiving palladium oxide thereupon in a controlled and uniform manner.

Still referring to FIG. 3 palladium oxide barrier layer 302 prevents a reaction between the catalytic metal and the silicon carbide 303 thus preventing degradation of the sensor and the formation of silicides. It is believed but not yet verified that some of the palladium oxide can be reduced to palladium with a possible, but not yet verified, increase in sensitivity.

Immediately following the barrier layer is a semiconductor substrate layer which may extend past the barrier interlayer in the horizontal direction for use in different applications such as a MOSFET transistor application. A voltage is applied across the top (catalytic sensing metal) and the bottom layers (silicon carbide semiconductor layer). A forward current moves from the catalytic sensing layer to the bottom silicon carbide semiconductor layer.

As used herein barrier is referred to as a chemical reaction barrier. In particular the palladium oxide barrier is a chemical reaction barrier. This is not to be confused with the potential barrier between the metal and semiconductor interface of a Schottky diode which is defined as the difference between the work function of the metal in electron volts and the electron affinity of the semiconductor also expressed in electron volts.

Figure 4:
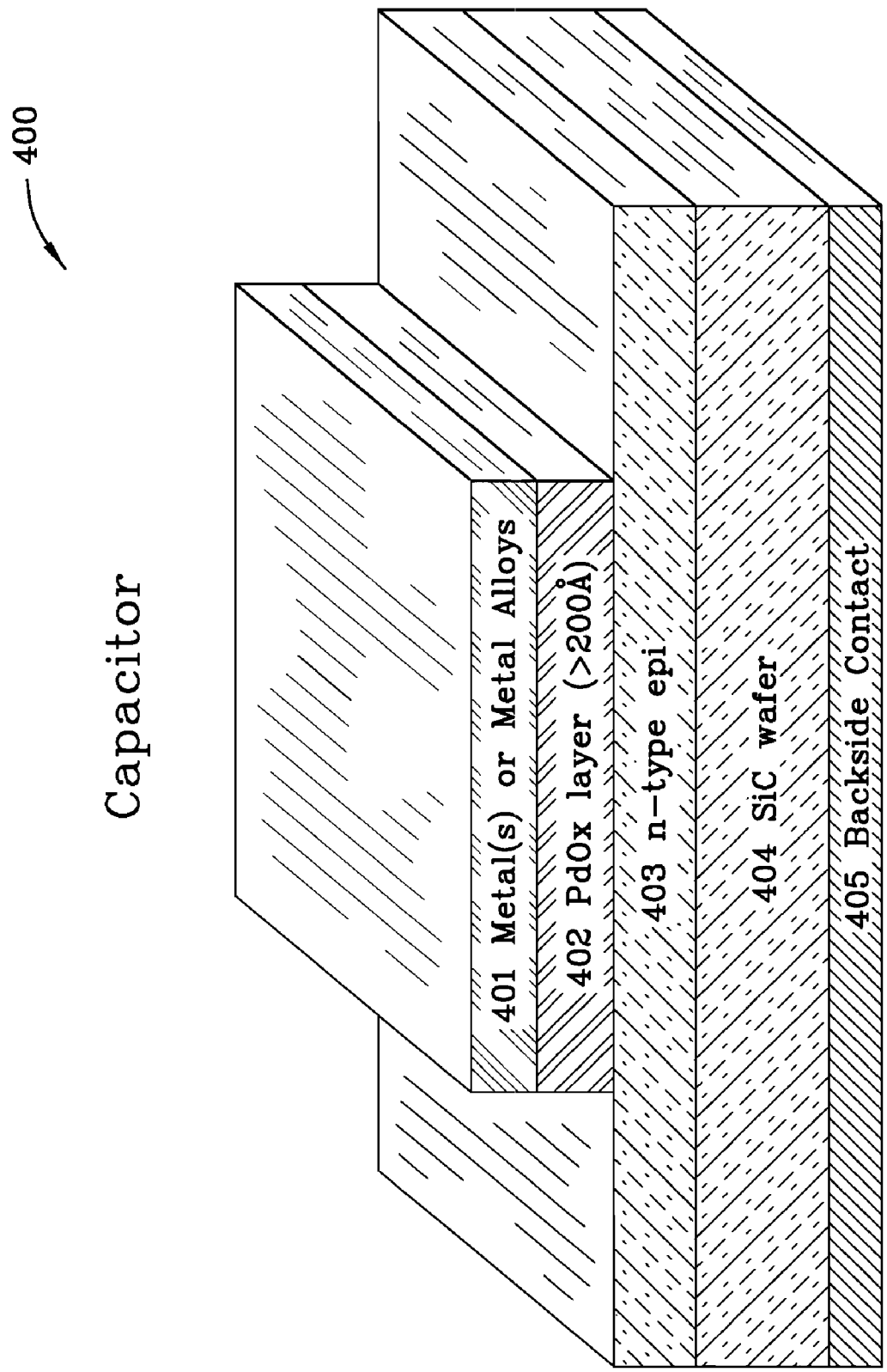
FIG. 4 is a cross-sectional view of the invention illustrating the metal layer, the palladium oxide interlayer, and the substrate layer used by way of example in a capacitor embodiment.

FIG. 4 is a representation of the capacitor embodiment 400 further illustrating the metal(s) or metal alloy(s) layer 401, the PdO$_x$ layer 402, n-type epitaxial layer 403, SiC wafer 404, and the backside contact 405. The metal(s) or metal alloy(s) layer 401 is located at the top of the device followed by the layer of palladium oxide 402 which has a thickness of at least 200 Angstroms. The n-type epitaxial layer 403 is located on top of the SiC wafer 404 followed by the backside contact 405. In this capacitor embodiment, the palladium oxide is not electrically conductive, and, therefore, no current flows through the device. The metal 401 is typically palladium or platinum. A voltage is applied across the sensor between the metals 501, 505 and the capacitance of the sensor is modulated by hydrogen or hydrocarbon interaction with the dipole moment formed at the interface of the metal 401 and the palladium oxide.

Figure 5:
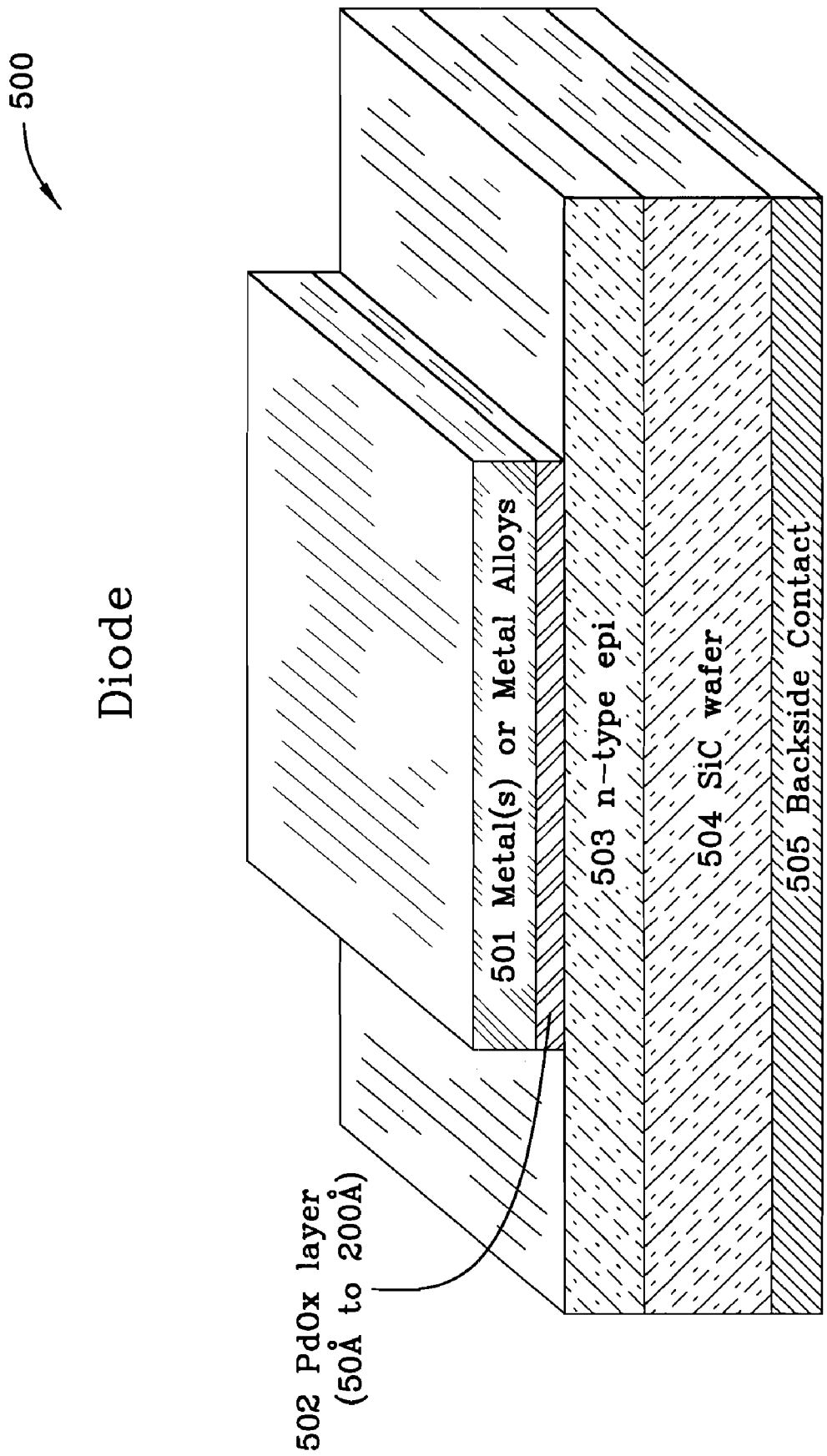
FIG. 5 is a cross-sectional view of the invention illustrating the catalytic metal layer, the palladium oxide barrier interlayer, and the substrate layer used by way of example in a diode embodiment.

FIG. 5 is a cross-sectional view of the diode 500 illustrating the metal(s) or metal alloys layer 501, the $PdO_x$ layer (50 Angstroms to 200 Angstroms in thickness) 502, n-type epitaxial layer 503 of the silicon carbide, SiC wafer 504, and the backside contact 505 similar to FIG. 3 absent the applied voltage. FIG. 5 illustrates the n-type epitaxial layer 503 of the silicon carbide. As stated previously, the silicon carbide is of the 6H, 4H, or 3C—SiC polytype.

Figure 6:
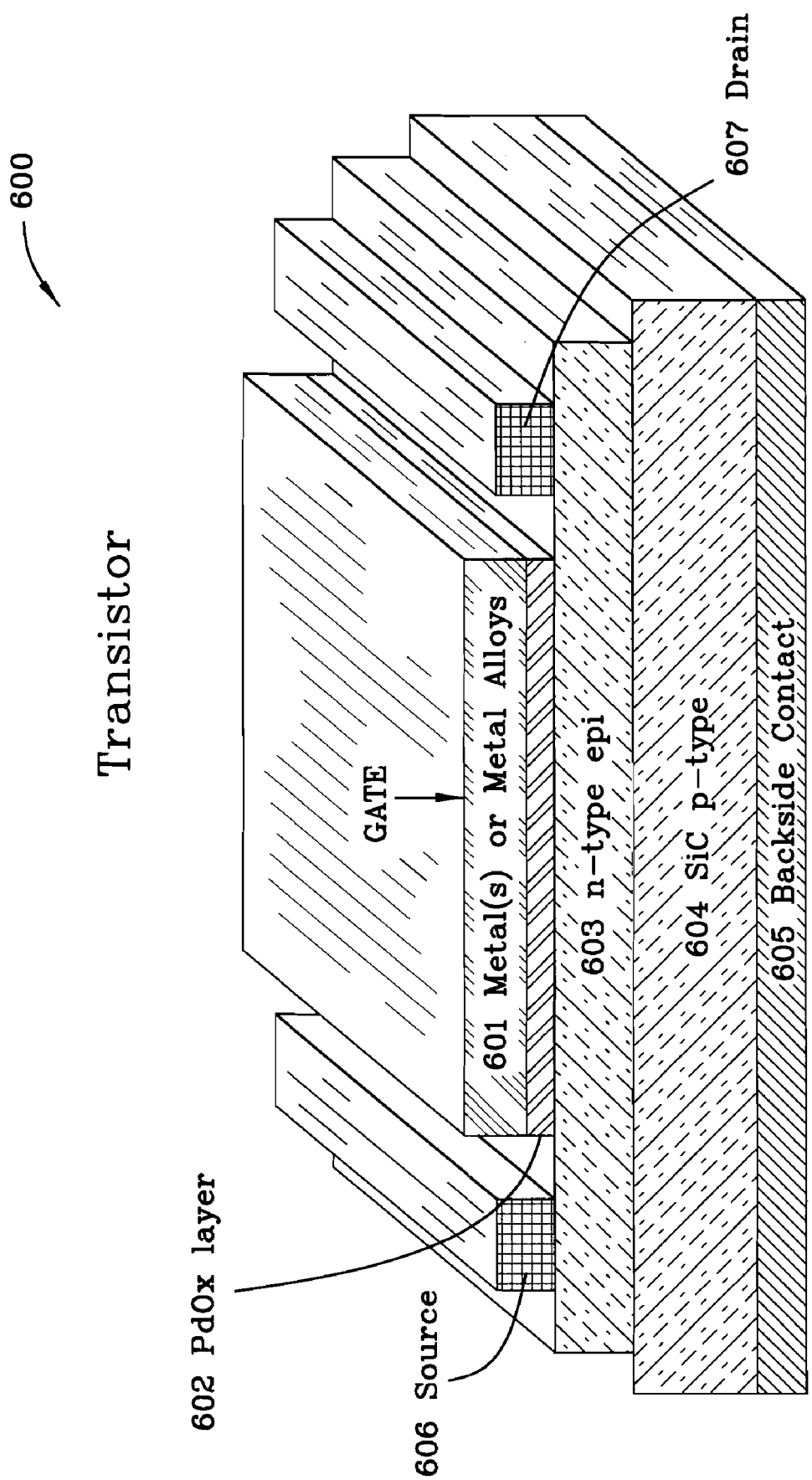
FIG. 6 is a cross-sectional view of the invention used by way of example illustrating the metal(s) or metal alloy gate layer, the palladium oxide layer, and the substrate layer in a transistor embodiment.

FIG. 6 is a cross-sectional view of the transistor 600 illustrating the metal(s) or metal alloys layer or gate 601, the palladium oxide layer 602, n-type epi layer 603 of the silicon carbide, SiC p-type 604, backside bias 605, a metallic source 606, and a metallic drain 607. The palladium oxide layer 602 is more than 200 Angstroms thick. For a given applied gate voltage, the presence of hydrogen modulates a channel formed in the n-type epilayer of the silicon carbide substrate controlling the flow of current between the source 606 and the drain 607. The source 606 and drain 607 are sometimes referred to herein as the first and second electrodes.

Figure 7:
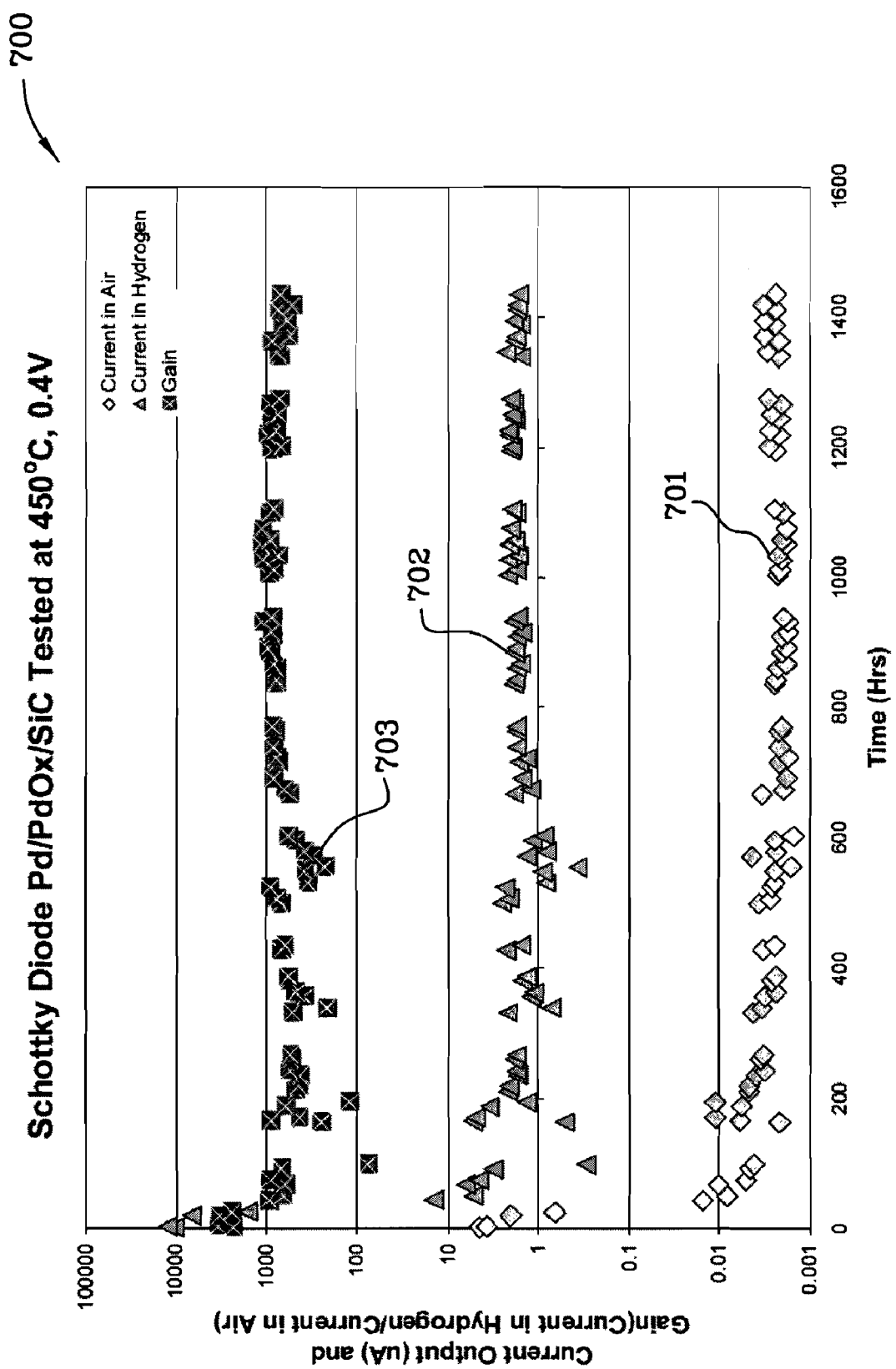
FIG. 7 is a graph of current output for air, 0.5% hydrogen in nitrogen and gain vs. time of the Schottky Diode Pd/PdO$_x$/SiC Tested at 450° C. with a forward bias of 0.4 VDC.

FIG. 7 illustrates current output in microamps of a Schottky diode consisting of a palladium/palladium oxide/silicon carbide structure tested at 450° C. with a forward current at a bias voltage of 0.4 VDC. FIG. 7 is a plot of current output (μA) of the diode of the invention at 450° C. with a forward bias of 0.4 VDC. Reference numeral 702 represents the current in the diode for hydrogen at 0.5% concentration and reference numeral 701 represents the current in the diode for air at 450° C. with a forward bias of 0.4 VDC. Gain 703 (current in hydrogen)/(current in air) vs. time up to 1400 hours of operation of the Schottky diode $Pd/PdO_x/SiC$ tested at 450° C. with a 0.4 VDC is also illustrated in FIG. 7. The plot illustrates stable measurement of the current in air and 0.5% hydrogen over a period of approximately 1400 hours of operation. The hydrogen was used along with nitrogen in the plot of FIG. 2. The high sensitivity and gain is illustrated by the plot of hydrogen 702 versus air 701.

Figure 8:
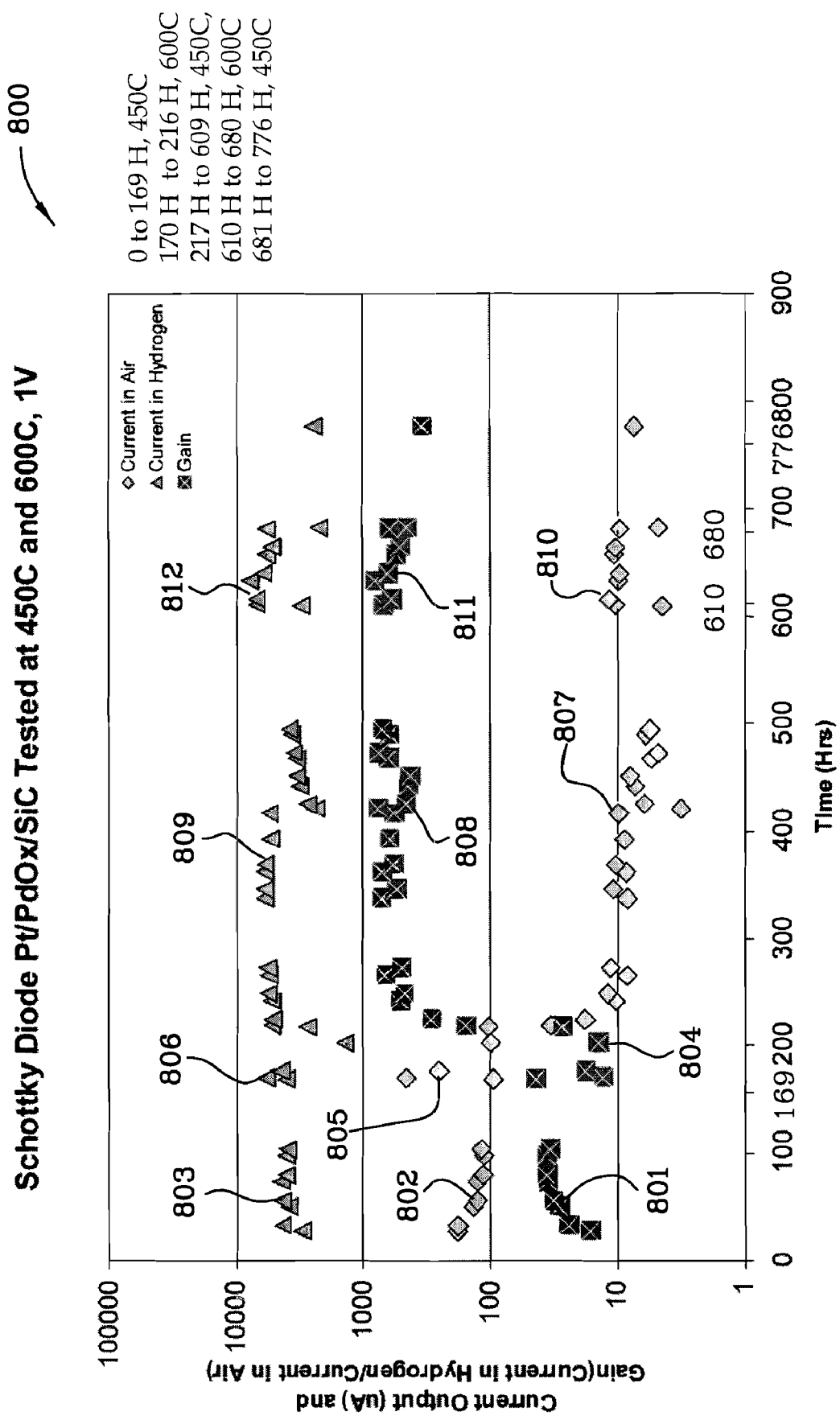
FIG. 8 is a graph of current output for air, 0.5% hydrogen in nitrogen and gain vs. time of the Schottky Diode Pt/PdO$_x$/SiC Tested at 450° C. and 600° C. with a forward bias of 1.0 VDC.

FIG. 8 illustrates the current output in microamps of a Schottky diode comprising a platinum/palladium oxide/silicon carbide structure tested at alternating temperatures of 450° C. and 600° C. with a forward bias voltage of 1.0 VDC. From 0 to 169 hours at 450° C. reference numeral 801 is the gain, reference numeral 802 is the current in air and reference numeral 803 is the current in hydrogen. From 170 to 216 hours at 600° C. reference numeral 804 is the gain, reference numeral 805 is the current in air, and reference numeral 806 is the current in hydrogen. From 217 to 609 hours at 450° C. reference numeral 807 is the current in air, reference numeral 808 is the gain, and reference numeral 809 is the current in hydrogen. From 610 to 680 hours at 600° C. reference numeral 810 is the current in air, reference numeral 811 is the gain, and reference numeral 812 is the current in hydrogen. Overall, although changes occurred in the baseline when the sensor is first introduced to 600° C. (a break-in period), FIG. 8 illustrates high gain, high sensitivity, and stability in the alternating temperature test over time.

The process steps of making the Schottky diode comprises the following steps: preparing a n-type semiconductor substrate layer (approximately 400 microns in thickness) of n-type silicon carbide (SiC) by cleaning, depositing back side contacts, applying photoresist and a Schottky diode photomask, controlled reactive sputter deposition (or evaporation) of approximately 50 Angstroms of palladium onto a target in an $O_2$ (oxygen) atmosphere on the silicon carbide substrate layer, and, sputter deposition of 450 Angstroms of a metal or metal alloy selected from the group consisting of Pt, Pd, Au, Ir, Ag, Ru, Rh, In, Os, Cr, Ti, and alloys of these metals with each other on top of said metal oxide layer. Alternatively, the palladium oxide may be evaporated onto the silicon carbide substrate. Lift off processes and etching is employed as necessary. The oxygen atmosphere may be withheld for a few seconds to prevent the formation of silicon dioxide on the silicon carbide.

Traditional photolithographic processes may be used to form sensors including the application of photoresist, masks, applying light to imidize portions of the photoresist, wet and dry etching, etc. The catalytic sensing layer and the barrier layer may also be deposited using the sol-gel method, reactive deposition, and chemical vapor deposition in addition to sputtering.

DESCRIPTION OF REFERENCE NUMERALS

100 . . . Prior art capacitor
100A . . . Capacitance-Voltage curves
100B . . . Dipole illustration
101 . . . Applied DC Voltage
102 . . . Ground potential
103 . . . Palladium
104 . . . Silicon dioxide insulator
104A . . . Dipole moment at the interface of palladium and silicon dioxide
105 . . . p type silicon
106 . . . Capacitance-Voltage curve without hydrogen
107 . . . Capacitance-Voltage with hydrogen
108 . . . Dipole
109 . . . Hydrogen
110 . . . Dipole represented as a differential voltage
200 . . . Current and voltage Sweep of $Pt/PdO_x/SiC$ at 450° C., 467 hours of operation
201 . . . Current measured in air
202 . . . Current measured in 0.5% hydrogen gas
200A . . . Current and voltage sweep of $Pd/PdO_x/SiC$ at 450° C., 715 hours of operation
201A . . . Current measured in air
202A . . . Current measured in 0.5% hydrogen gas
300 . . . Gas Detecting Diode with Applied Voltage
301 . . . Metal(s) or Metal Alloy(s) Layer
302 . . . $PdO_x$ (barrier Layer)
303 . . . SiC Layer
304 . . . Backside Contact
305 . . . Amp meter
306 . . . Voltage polarity reference
307 . . . Voltage polarity reference
308 . . . DC Voltage
309 . . . Hydrocarbons
310 . . . Hydrogen
400 . . . Capacitor
401 . . . Metal(s) or Metal Alloys Layer
402 . . . $PdO_x$ Layer
403 . . . n-type epi Layer
404 . . . SiC wafer
405 . . . Backside Contact 500 ... Diode
501 ... Metal(s) or Metal Alloys Layer
502 ... $PdO_x$ Layer
503 ... n-type epi Layer
504 ... SiC wafer
505 ... Backside Contact
600 ... Transistor
601 ... Metal(s) or Metal Alloy(s) Layer
602 ... $PdO_x$ Layer
603 ... n-type epi layer
604 ... SiC p-type
605 ... Backside contact
606 ... Source
607 ... Drain
700 ... Graph of Current Output (Hydrogen and Air) and Gain vs. Time for Schottky Diode Pd/$PdO_x$/SiC
701 ... Current in air
702 ... Current in Hydrogen
703 ... Gain
800 ... Graph of Current Output and Gain vs. Time for Schottky Diode Pt/$PdO_x$/SiC
801 ... Gain 0 to 169 hours, 450° C.
802 ... Current in air, 0 to 169 hours, 450° C.
803 ... Current in 0.5% hydrogen, 0 to 169 hours, 450° C.
804 ... Gain 170 to 216 hours, 600° C.
805 ... Current in air, 170 to 216 hours, 600° C.
806 ... Current in 0.5% hydrogen, 170 to 216 hours, 600° C.
807 ... Current in air, 217 to 609 hours, 450° C.
808 ... Gain 217 to 609 hours, 450° C.
809 ... Current in hydrogen, 217 to 609 hours, 450° C.
810 ... Current in air, 610 to 680 hours, 600° C.
811 ... Gain, 610 to 680 hours, 600° C.
812 ... Current in hydrogen, 610 to 680 hours, 600° C.

Although this invention has been described by way of example and with particularity and specificity, those skilled in the art will recognize that many changes and modifications may be made without departing from the spirit and scope of the invention defined by the Claims which follow hereinbelow.

We claim:

1. A process for fabricating a high temperature gas sensor comprising the steps of:
   sputtering, in a controlled manner, Pd in an $O_2$ atmosphere on a SiC substrate layer forming a $PdO_x$ layer on said SiC substrate;
   depositing, by sputtering a metal selected from the group consisting of Pt, Pd, Au, Ir, Ag, Ru, Rh, In, Os, Cr, and Ti on said $PdO_x$ layer; and,
   depositing an electrode on said SiC substrate.

2. A process for fabricating a high temperature gas sensor as claimed in claim 1 wherein said step of sputtering, in a controlled manner, Pd in an $O_2$ atmosphere on a SiC substrate layer forming a $PdO_x$ layer on said SiC substrate continues to a thickness of approximately 50 to 200 Angstroms.

3. A process for fabricating a high temperature gas sensor as claimed in claim 1 wherein said step of sputtering, in a controlled manner, Pd in an $O_2$ atmosphere on a SiC substrate layer forming a $PdO_x$ layer on said SiC substrate continues to a thickness of greater than 200 Angstroms.

4. A process for fabricating a high temperature gas sensor as claimed in claim 1 further comprising the step of depositing a plurality of electrodes on said SiC substrate.

5. A process for fabricating a high temperature gas sensor as claimed in claim 1 wherein said SiC substrate layer is approximately 400 microns thick.

6. A process for fabricating a high temperature gas sensor as claimed in claim 1 wherein said step of depositing, by sputtering a metal selected from the group consisting of Pt, Pd, Au, Ir, Ag, Ru, Rh, In, Os, Cr, and Ti on said $PdO_x$ layer, is performed by alloying said selected metal with a metal selected from the group consisting of Pt, Pd, Au, Ir, Ag, Ru, Rh, In, Os, Cr, and Ti.

7. A method for using a Schottky diode in an atmosphere containing hydrogen and/or hydrocarbons, comprising the steps of: applying bias voltage across the top and bottom layers of said Schottky diode wherein said diode includes a top metal layer selected from the group consisting of Pt, Pd, Au, Ir, Ag, Ru, Rh, In, Os, Cr, and Ti or alloy of any two or more of the group, a $PdO_x$ barrier interlayer, said $PdO_x$ barrier interlayer is approximately 50 to 200 Angstroms thick an n-type SiC substrate layer, and an electrode engaging said SiC substrate layer forming a backside contact; and, measuring the current through the diode which varies as a function of the hydrogen and/or hydrocarbon content.

8. A method for using a Schottky diode in an atmosphere containing hydrogen and/or hydrocarbons as claimed in claim 7 wherein said top metal layer is approximately 150 to 1000 Angstroms thick.

9. A method for using a capacitor in an atmosphere containing hydrogen and/or hydrocarbons, comprising the steps of: applying bias voltage across the capacitor comprising a top metal layer selected from the group consisting of Pt, Pd, Au, Ir, Ag, Ru, Rh, In, Os, Cr, and Ti or alloy of any two or more of the group, a dielectric $PdO_X$ barrier interlayer, said dielectric $PdO_x$ barrier interlayer is greater than 200 Angstroms thick, an n-type SiC substrate layer, and an electrode engaging said SiC substrate layer forming a backside contact; and, measuring the capacitance which varies as a function of the hydrogen and/or hydrocarbon content.

10. A method for using a capacitor in an atmosphere containing hydrogen and/or hydrocarbons as claimed in claim 9 wherein said top metal layer is approximately 150 to 1000 Angstroms thick.

11. A method for using a transistor in an atmosphere containing hydrogen and/or hydrocarbons, comprising the steps of: applying voltage across a top gate metal layer selected from the group consisting of Pt, Pd, Au, Ir, Ag, Ru, Rh, In, Os, Cr, and Ti or alloy of any two or more of the group and an n-type SiC substrate layer, a dielectric $PdO_X$ barrier interlayer residing between said top gate metal layer and said n-type SiC substrate layer, said dielectric $PdO_X$ barrier interlayer is greater than 200 Angstroms thick; applying a voltage across first and second electrodes engaging said SiC substrate layer enabling current to flow a channel in said SiC substrate; and, measuring said current flow in said channel which varies as a function of the hydrogen content.

12. A method for using a transistor in an atmosphere containing hydrogen and/or hydrocarbons as claimed in claim 11 wherein said top metal layer is approximately 150 to 1000 Angastroms thick.

13. A process for fabricating a high temperature gas sensor comprising the steps of;
   evaporating, in a controlled manner, Pd in an $O_2$ atmosphere on a SiC substrate layer forming a $PdO_x$ layer on said SiC substrate;
   depositing, by sputtering a metal selected from the group consisting of Pt, Pd, Au, Ir, Ag, Ru, Rh, In, Os, Cr, and Ti on said $PdO_x$ layer; and,
   depositing an electrode on said SiC substrate.

* * * * *